United States Patent
Huang et al.

(10) Patent No.: US 12,042,272 B2
(45) Date of Patent: Jul. 23, 2024

(54) INSERTION MODULE AND INSERTION DEVICE HAVING THE SAME

(71) Applicant: BIONIME CORPORATION, Taichung (TW)

(72) Inventors: Chun-Mu Huang, Taichung (TW); Chieh-Hsing Chen, Taichung (TW); Kuan-Lin Chang, Taichung (TW)

(73) Assignee: BIONIME CORPORATION, Taichung (TW)

( * ) Notice: Subject to any disclaimer, the term of this patent is extended or adjusted under 35 U.S.C. 154(b) by 294 days.

(21) Appl. No.: 16/944,693

(22) Filed: Jul. 31, 2020

(65) Prior Publication Data

US 2021/0030969 A1 Feb. 4, 2021

Related U.S. Application Data

(60) Provisional application No. 62/882,140, filed on Aug. 2, 2019.

(51) Int. Cl.
*A61B 5/145* (2006.01)
*A61B 5/00* (2006.01)
(Continued)

(52) U.S. Cl.
CPC ........ *A61B 5/14503* (2013.01); *A61B 5/0002* (2013.01); *A61B 5/0004* (2013.01);
(Continued)

(58) Field of Classification Search
CPC .............. A61B 5/14503; A61B 5/6849; A61B 2560/063; A61B 5/0002; A61B 5/0004; A61B 5/14532; A61B 5/14546; A61B 5/14865; A61B 5/6801; A61B 5/6867; A61B 5/688; A61B 5/1451; A61B 2560/045; A61B 2562/0295;
(Continued)

(56) References Cited

U.S. PATENT DOCUMENTS

| 10,413,183 B2 * | 9/2019 | Antonio ............... A61B 5/1486 |
| 2005/0101912 A1 | 5/2005 | Faust et al. |

(Continued)

FOREIGN PATENT DOCUMENTS

| WO | 2018222012 A1 | 12/2018 | |
| WO | WO-2018222012 A1 * | 12/2018 | ......... A61B 17/3468 |

OTHER PUBLICATIONS

WO2018222012A1_Descripion (Translation) (Year: 2018).*
(Continued)

*Primary Examiner* — Jay B Shah
*Assistant Examiner* — Meghan R Kumar
(74) *Attorney, Agent, or Firm* — Perkins Coie LLP; Sean Lee; Viola Kung

(57) ABSTRACT

A insertion module includes a main body, an auxiliary insertion seat, an insertion needle assembly and a sensor assembly. The main body has a plurality of slide grooves. The auxiliary insertion seat has a base portion, and a plurality of wing portions. The insertion needle assembly is fixed through the interference between the wing portions and wall surfaces of the slide grooves, such that the insertion needle is prevented from being oblique to an insertion direction before the insertion needle is inserted into a host.

18 Claims, 20 Drawing Sheets

(51) Int. Cl.
*A61B 5/1486* (2006.01)
*H01R 12/73* (2011.01)

(52) U.S. Cl.
CPC ...... *A61B 5/14532* (2013.01); *A61B 5/14546* (2013.01); *A61B 5/14865* (2013.01); *A61B 5/6801* (2013.01); *A61B 5/6849* (2013.01); *A61B 5/6867* (2013.01); *A61B 5/688* (2013.01); *A61B 5/1451* (2013.01); *A61B 2560/045* (2013.01); *A61B 2560/063* (2013.01); *A61B 2562/0295* (2013.01); *A61B 2562/14* (2013.01); *A61B 2562/16* (2013.01); *A61B 2562/166* (2013.01); *A61B 2562/168* (2013.01); *A61B 2562/225* (2013.01); *A61B 2562/226* (2013.01); *A61B 2562/227* (2013.01); *H01R 12/737* (2013.01)

(58) Field of Classification Search
CPC ............ A61B 2562/14; A61B 2562/16; A61B 2562/166; A61B 2562/168; A61B 2562/225; A61B 2562/226
See application file for complete search history.

(56) References Cited

U.S. PATENT DOCUMENTS

| | | |
|---|---|---|
| 2012/0209187 A1 | 8/2012 | Kamen et al. |
| 2017/0290535 A1 | 10/2017 | Rao et al. |
| 2018/0235520 A1* | 8/2018 | Rao ..................... A61B 5/6849 |
| 2019/0201638 A1 | 7/2019 | Kamen et al. |

OTHER PUBLICATIONS

WO-2018222012-A1_Description(Translation Attached) (Year: 2018).*
Search Report, which was issued to European Application No. 20189219.7 by the EPO on Nov. 17, 2020.

* cited by examiner

INSERTION MODULE AND INSERTION DEVICE HAVING THE SAME

CROSS-REFERENCE TO RELATED APPLICATION

This application claims priority of U.S. Provisional Patent Application No. 62/882,140, filed on Aug. 2, 2019.

FIELD

The disclosure relates to an insertion device, and more particularly to an insertion module for inserting an glucose sensor into a host and an insertion device having the same.

BACKGROUND

A conventional insertion device disclosed in U.S. patent Ser. No. 10/413,183 is for inserting a biosensor into a host, and includes a plunger, and a piercing assembly to which a sensor assembly is mounted.

The piercing assembly is inserted into the host upon depression of the plunger, and is retracted from the host when the plunger is released. During the insertion and retraction operations, the piercing assembly may be obliquely inserted into the host, and may therefore be obliquely retracted from the host to cause discomfort of the host.

SUMMARY

Therefore, an object of the disclosure is to provide a insertion module that can alleviate at least one of the drawbacks of the prior art.

According to the disclosure, the insertion module is adapted to to guide an insertion needle to move stably before inserting into a host, and includes a main body, an auxiliary insertion seat, an insertion needle assembly and a sensor assembly. The main body has an accommodating hole that extends along an axial line, and a plurality of slide grooves that are disposed on the accommodating hole around the axial line and communicate with the accommodating hole. The auxiliary insertion seat has a base portion, and a plurality of wing portions that are connected to the base portion. Each of the wing portions is reciprocated within a respective one of the slide grooves, and has a protruding portion. The insertion needle assembly includes a needle seat assembled with the base portion of the auxiliary insertion seat, and an insertion needle that is connected to the needle seat. A distance between a tip end of the insertion needle and a skin surface of the host is defined as an initial stroke distance. The sensor assembly includes a sensing seat, and a sensor that is held within the sensing seat. The sensing seat is assembled with the base portion of the auxiliary insertion seat. The insertion needle is inserted through the sensing seat to cover the sensor. Each of the slide grooves has a wall surface. The protruding portion of each of the wing portions resiliently abuts against the wall surface of a respective one of the slide grooves in point-contact such that the auxiliary insertion seat is fixed before inserting into the host through the interference between the protruding portions and the wall surfaces to provide a stable inserting and prevent the insertion needle from oblique in said initial stroke distance.

Another object of the disclosure is to provide a insertion device that can alleviate at least one of the drawbacks of the prior art.

According to the disclosure, the insertion device includes an actuation module and an insertion module. The actuation module includes a cover body, a main cover received in the cover body, an insertion seat connected to the main cover, a first elastic member abutting against the main cover and the insertion seat, a retraction seat disposed between the main cover and the insertion seat, and a second elastic member abutting against the retraction seat and the insertion seat. The insertion module includes a main body, an auxiliary insertion seat, an insertion needle assembly and a sensor assembly. The main body has an accommodating hole that extends along an axial line, and a plurality of slide grooves disposed on the accommodating hole around the axial line and communicating with the accommodating hole. The auxiliary insertion seat has a base portion, and a plurality of wing portions that are connected to the base portion. Each of the wing portions is reciprocated within a respective one of the slide grooves, and has a protruding portion. The insertion needle assembly includes a needle seat assembled with the base portion of the auxiliary insertion seat, and an insertion needle connected to the needle seat. A distance between a tip end of the insertion needle and a skin surface of a host is defined as an initial stroke distance. The sensor assembly includes a sensing seat, and a sensor held within the sensing seat. The sensing seat is assembled with the seat body of the auxiliary insertion seat, and the insertion needle is inserted through the sensing seat to cover the sensor. Each of the slide grooves has a wall surface. The protruding portion of each of the wing portions resiliently abuts against the wall surface of a respective one of the slide grooves in point-contact such that the auxiliary insertion seat is fixed before inserting into the host through the interference between the protruding portions and the wall surfaces to provide a stable inserting and prevent the insertion needle from oblique in the initial stroke distance.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
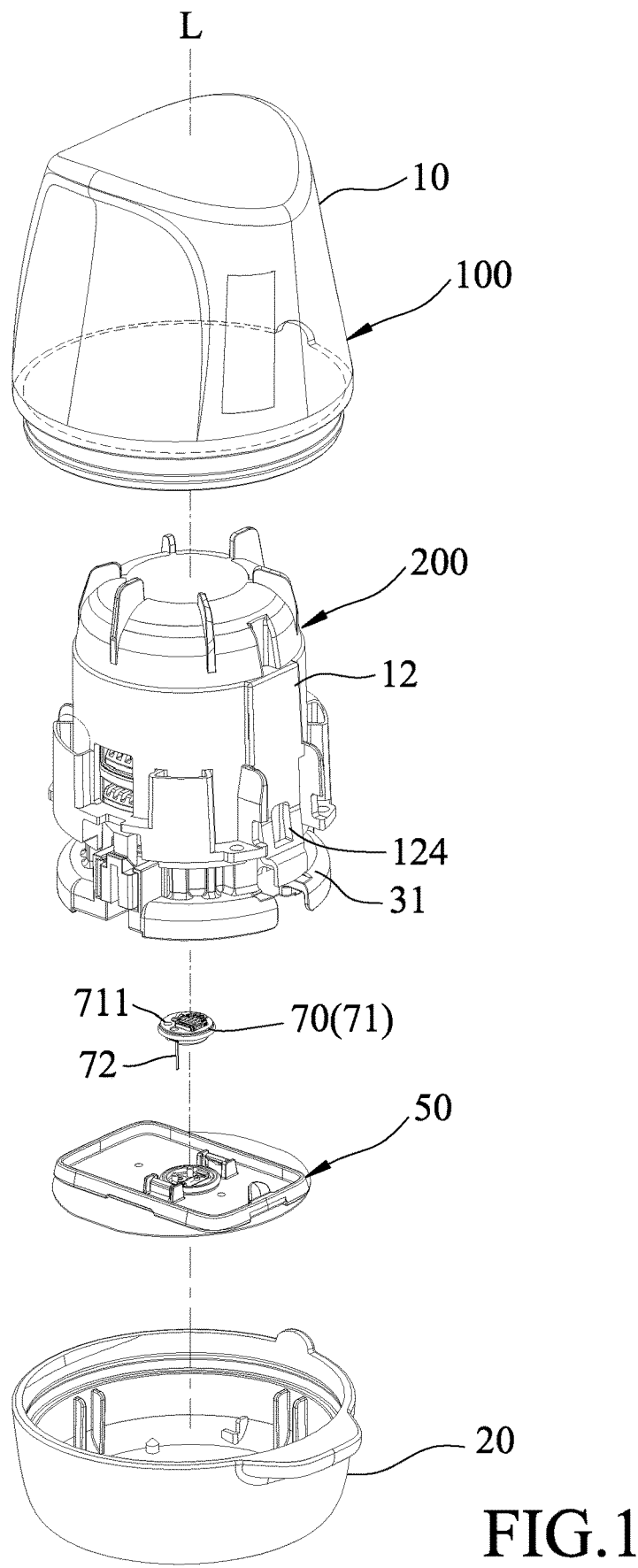
FIG. 1 is an exploded perspective view illustrating a first embodiment of the insertion device according to the disclosure.
Figure 2:
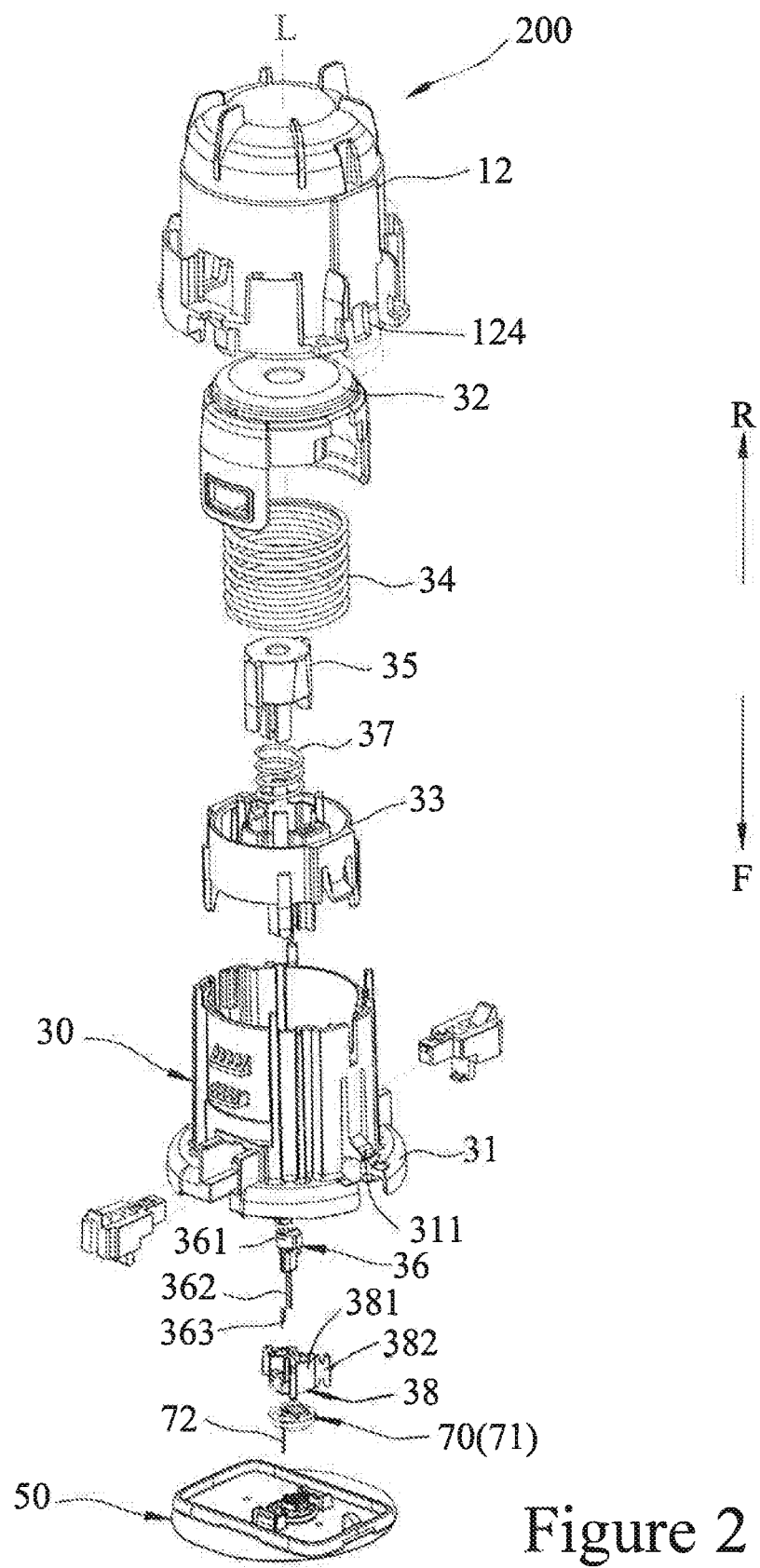
FIG. 2 is a fragmentary exploded perspective view illustrating the first embodiment.

Before the disclosure is described in greater detail, it should be noted that where considered appropriate, reference numerals or terminal portions of reference numerals have been repeated among the figures to indicate corresponding or analogous elements, which may optionally have similar characteristics.

Referring to FIGS. 1 to 5, the first embodiment of the insertion device according to the disclosure is able to guide an insertion needle to move stably before inserting into a host, and includes a limiting member 100, an actuation unit 200 and an insertion module 30.

The limiting member 100 includes an upper casing 10, and a lower casing 20 that is able to be tightly coupled to the upper casing 10.

The actuation module 200 includes a cover body 12 that is disposed in the upper casing 10, a main cover 32 that is received in the cover body 12, an insertion seat 33 that is connected to the main cover 32, a first elastic member 34 abutted against the main cover 32 and the insertion seat 33, a retraction seat 35 that is disposed between the main cover 32 and the insertion seat 33, and a second elastic member 37 abutted against the retraction seat 35 and the insertion seat 33. The cover body 12 has a pair of lining engaging structures 124 at a bottom portion thereof. The first elastic member 34 and the second elastic member 37 may be configured as pre-compressed springs. The cover body has a pair of urging portions 123 on an inner surrounding surface thereof. The main cover 32 has a limiting member 323 that extends toward the insertion seat 33. The insertion seat 33 has a pair of barb-shaped retraction positioning portions 334, and a pair of buckle portions 335 that are able to be respectively pushed by the urging portions 123 of the cover body 12.

The insertion module 30 is able to guide the insertion needle to move stably before the insertion needle is inserted into the host, and includes a main body 31, an auxiliary insertion seat 38, an insertion needle assembly 36, a base 50 and a sensor assembly 70.

The main body 31 has a pair of body engaging structures 311 that are able to respectively engage with the lining engaging structures 124 of the cover body 12, an accommodating hole 312 that extends along an axial line (L), a plurality of slide grooves 313 disposed on the accommodating hole 312 around the axial line (L) and communicating with the accommodating hole 312, and a pair of stopping portion 314. The buckle portions 335 of the insertion seat 33 respectively and separably abut against the stopping portions 314 of the main body 31 so as to form an insertion limiting structure (A) (see FIG. 4). The slide grooves 313 are equally spaced apart from each other around the axial line (L). In this embodiment, the number of the slide grooves 313 is three. Each of the slide grooves 313 has a wall surface 315 (see FIG. 4) that is gradually widened along an insertion direction (F). The the wall surface 315 of each of the slide grooves 313 includes an included angle between the axial line (L) from 0 degree to 3 degrees.

The auxiliary insertion seat 38 has a base portion 381, a plurality of wing portions 382 that are connected to the base portion 381, and a plurality of coupling protrusions 383 that protrude from a bottom surface of the base portion 381. The base portion 381 is movable along the accommodating hole 312. Each of the wing portions 382 is movable along a respective one of the slide grooves 313. Each of the wing portions 382 has a protruding portion 385 that resiliently abutted against the wall surface 315 of the respective one of the slide grooves 313 in point-contact. Each of the wing portions 382 has two notches 384 and is H-shaped. The notches 384 of each wing portion 382 are respectively formed at top and bottom portions of the wing portion 382, such that each wing portion 382 provides a restoring force in a radially outward direction after being compressed in a radial direction of the auxiliary insertion seat 38 perpendicular to the axial line (L). The wing portions 382 of the auxiliary insertion seat 38 are equally spaced apart from each other around the axial line (L). In a modification, the number of the wing portion 382 may be two, and the wing portions 382 are equally spaced apart from each other by 180 degrees.

Figure 18:
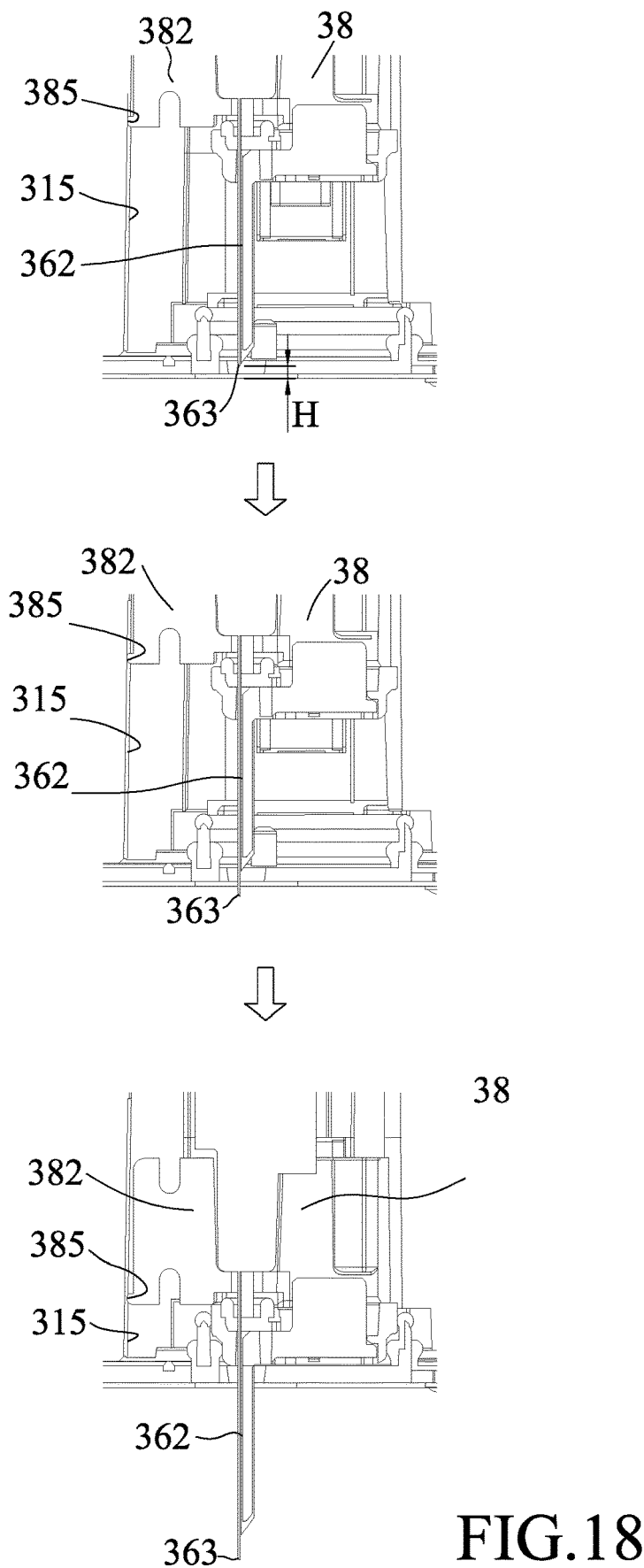
FIG. 18 is a schematic view illustrating an insertion operation of the first embodiment.

The insertion needle assembly 36 includes a needle seat 361 that is mounted between the retraction seat 35 and the base portion 381 of the auxiliary insertion seat 38, and an insertion needle 362 that is connected to the needle seat 361. The needle seat 361 and the retraction seat 35 are able to be separated from each other so as to prevent misalignment therebetween due to manufacturing tolerance. Referring to FIG. 18, the distance between a tip end 363 of the insertion needle 362 and the skin surface of the host is defined as an initial stroke distance (H). In this embodiment, the initial stroke distance (H) is no greater than 1 millimeter.

The base 50 is separably positioned at a bottom portion of the main body 31, and is able to be adhered to the skin surface via an adhesive pad.

The sensor assembly 70 includes a sensing seat 71, and a sensor 72 held within the sensing seat 71. The sensing seat 71 has a plurality of coupling recesses 711 that permit the coupling protrusions 383 of the auxiliary insertion seat 38 to engage therewith. The insertion needle 362 is inserted through the sensing seat 71 to cover the sensor 72.

Figure 3:
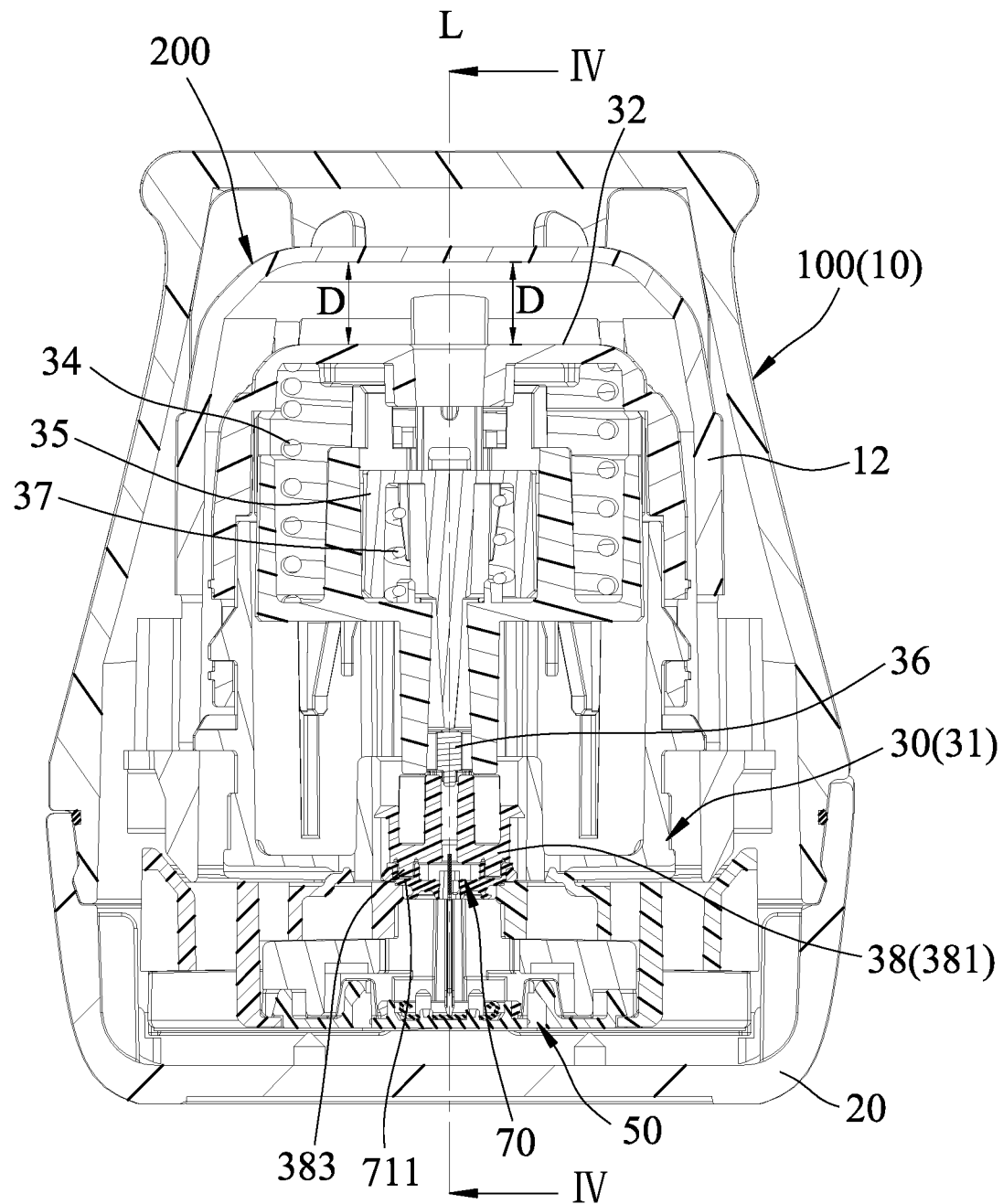
FIG. 3 is a sectional view illustrating the first embodiment in an initial state.
Figure 4:
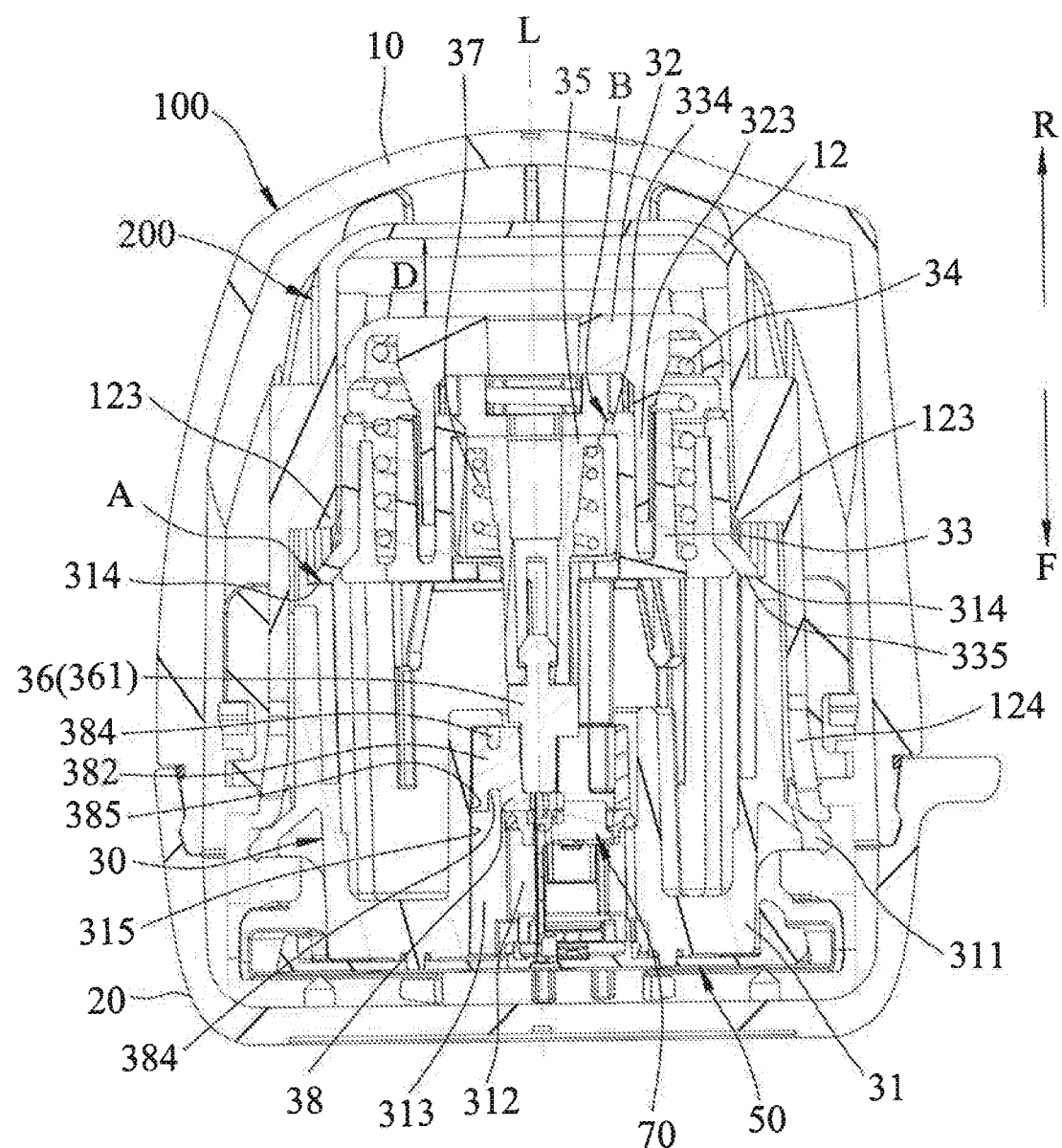
FIG. 4 is a sectional view taken along line IV-IV in FIG. 3.
Figure 5:
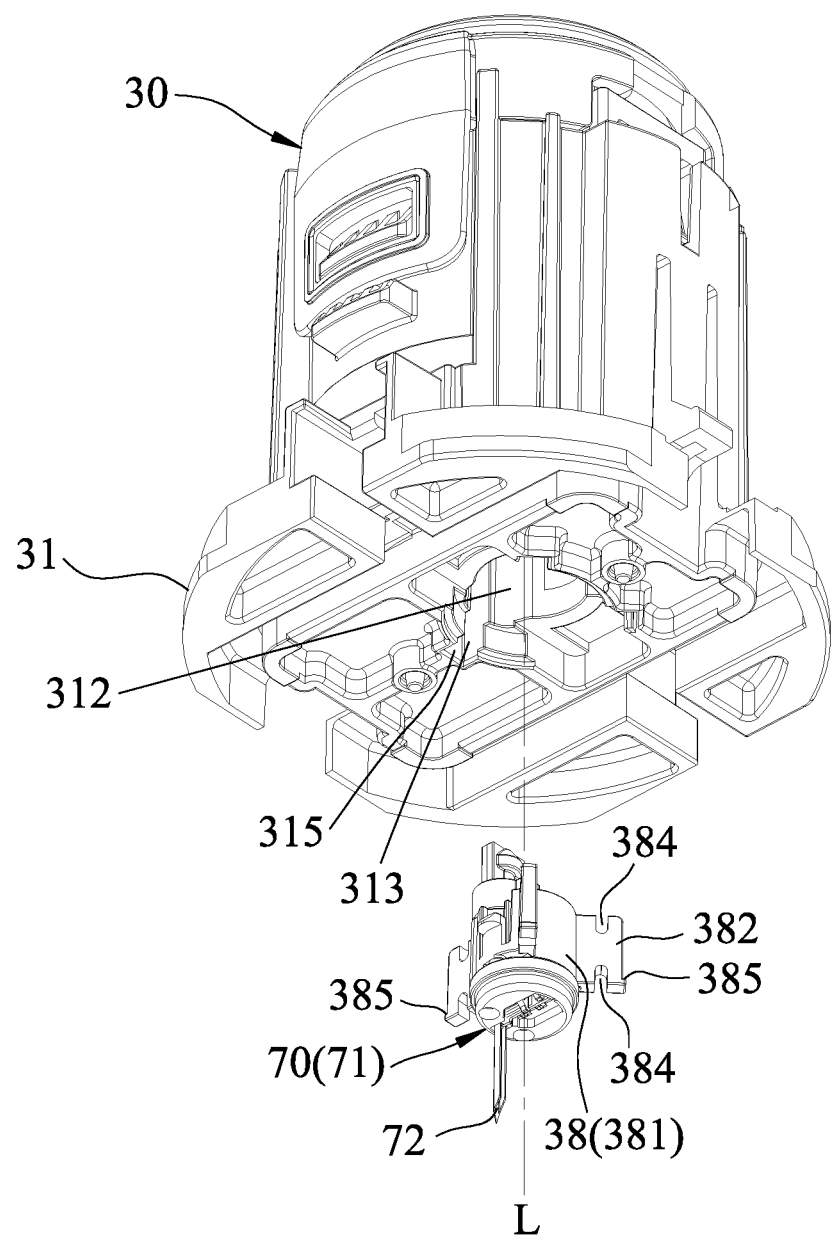
FIG. 5 is a bottom exploded perspective view illustrating the first embodiment.

Referring to FIGS. 3 and 4, after the first embodiment of the insertion device is assembled, the upper portion 302 and the lower portion 303 of the main body assembly 300 are interconnected, a top portion of the cover body 12 and a top portion of the main cover 32 are spaced apart from each other by a distance (D) (see FIG. 3), the buckle portions 335 of the insertion seat 33 respectively abut against the stopping portions 314 of the main body 31 so as to position the insertion seat 33 at a pre-insertion position, the first elastic member 34 is pre-compressed between the insertion seat 33 and the main cover 32 to generate a restoring force, the second elastic member 37 is pre-compressed between the retraction seat 35 and the insertion seat 33 to generate a restoring force, the retraction positioning portion 334 of the insertion seat 33 is limited by the limiting member 323 of the main cover 32 so that the retraction seat 35 is at a pre-insertion position, the coupling protrusions 383 of the auxiliary insertion seat 38 is fitted into the coupling recesses 711 of the sensing seat 71 so that the sensing seat 71 and the auxiliary insertion seat 38 are interconnected, the auxiliary insertion seat 38 is connected to the needle seat 361 of the insertion needle assembly 36 so that the insertion needle assembly 36 is retained in the main body 31 and is shielded by the base 50, and the base 50 is positioned relative to the main body 31. The retraction positioning portions 334 of the insertion seat 33 is removably limited by the limiting member 323 of the main cover, so as to form a retraction limiting structure (B) (see FIG. 4) that positions the retraction seat 35 relative to the insertion seat 33.

Figure 6:
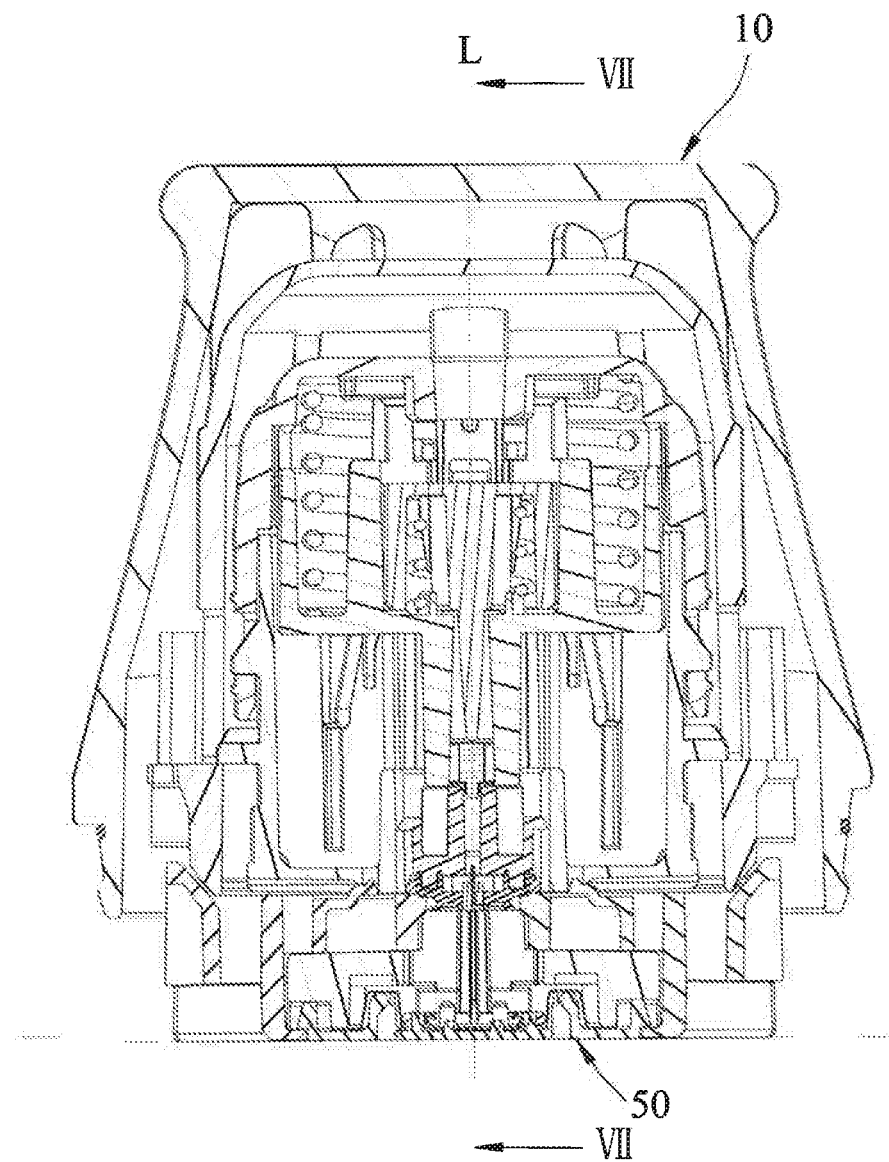
FIG. 6 is a sectional view illustrating a lower casing of the first embodiment being removed.
Figure 7:
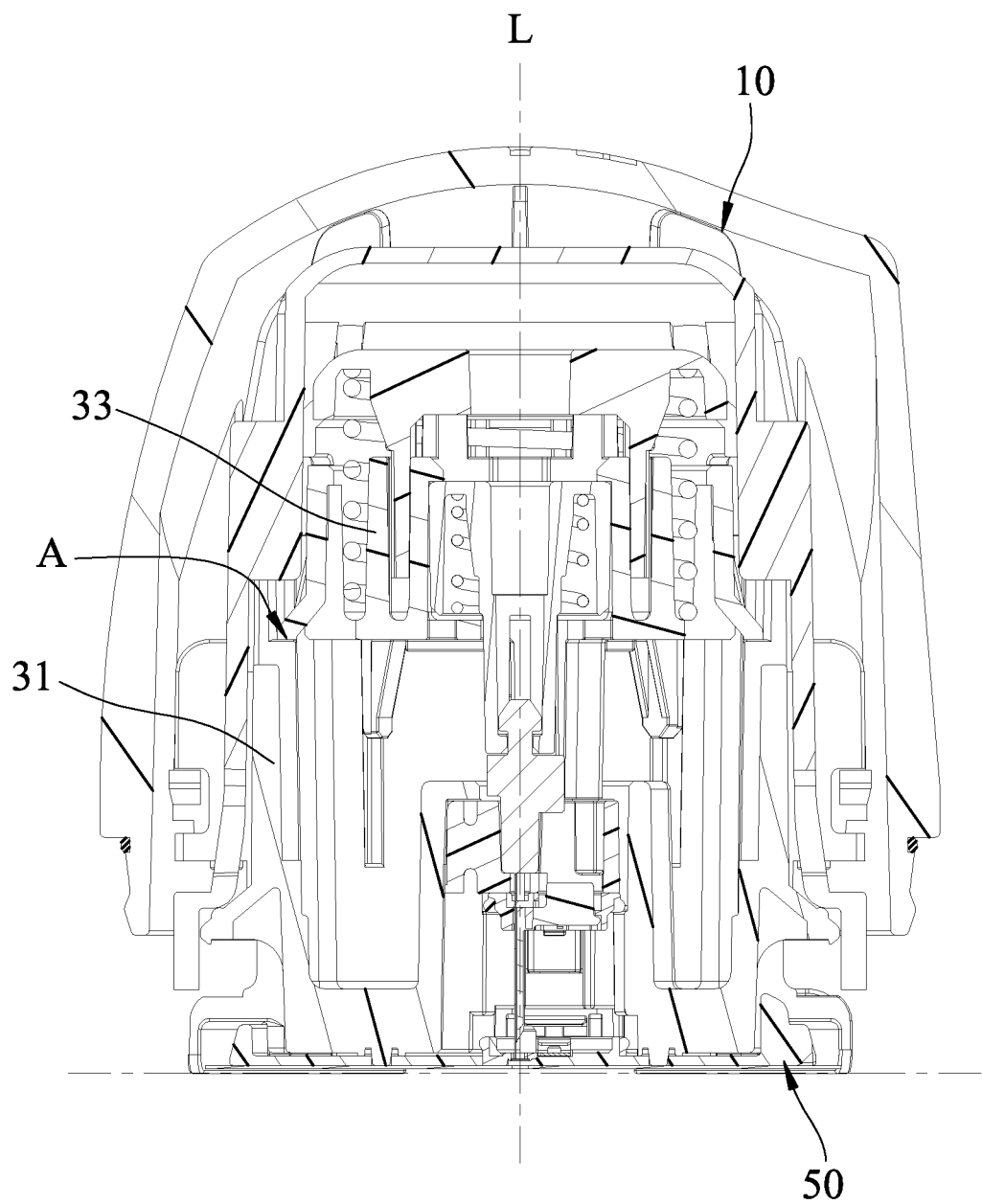
FIG. 7 is a sectional view taken along line VII-VII in FIG. 6.
Figure 8:
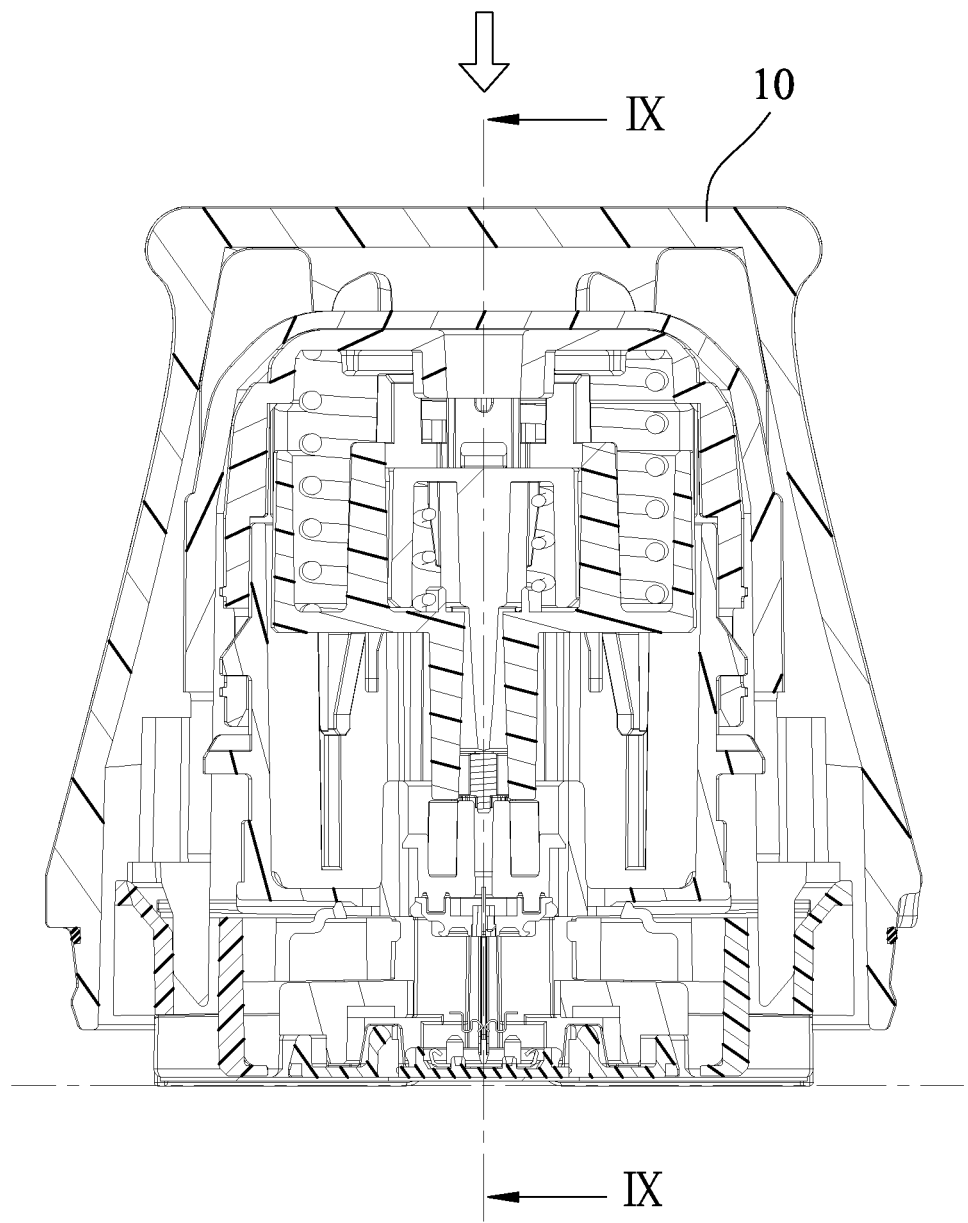
FIG. 8 is a sectional view illustrating an upper casing of the first embodiment being depressed.
Figure 9:
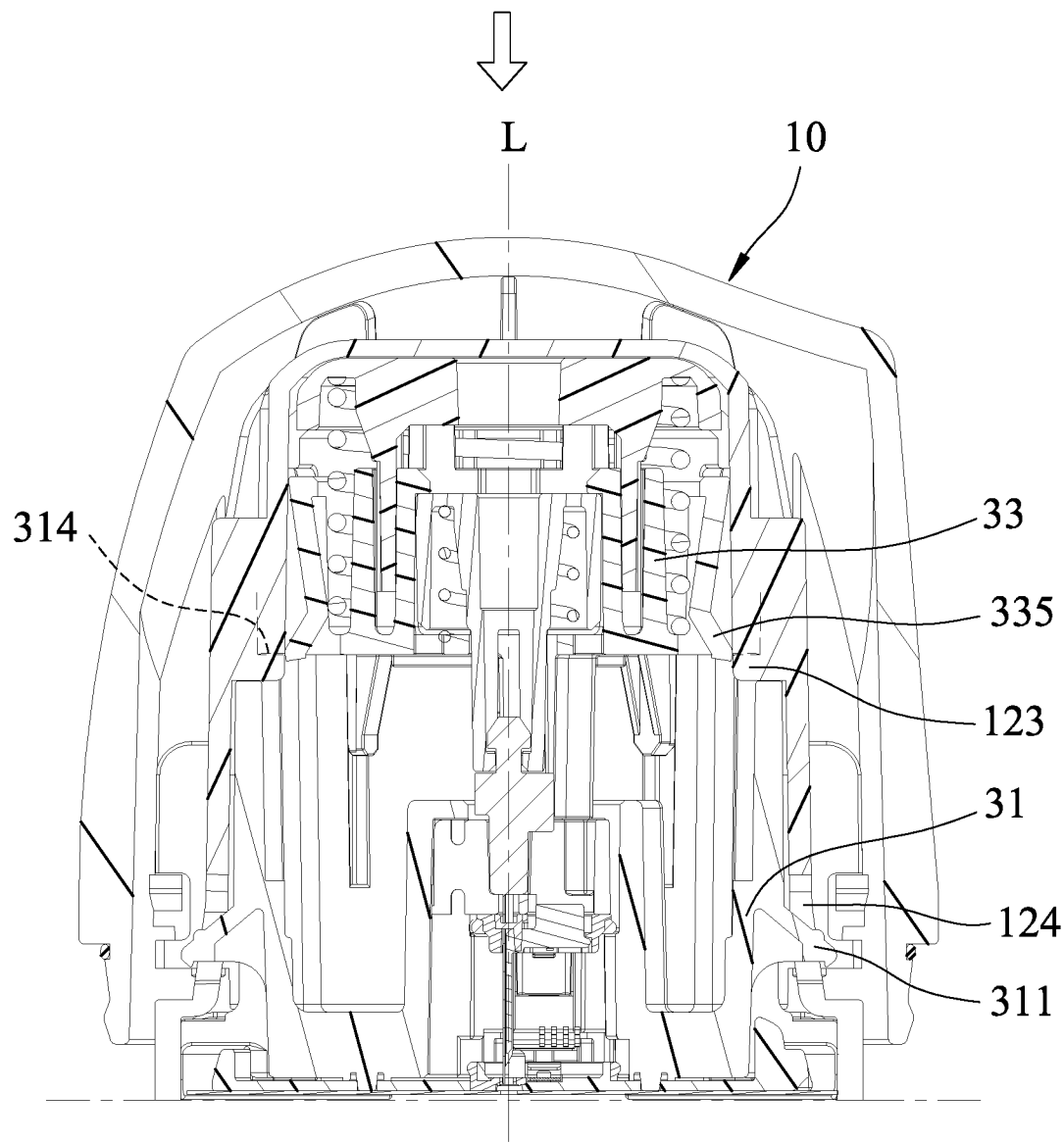
FIG. 9 is a sectional view taken along line IX-IX in FIG. 8.

Referring to FIGS. 6 and 7, the base 50 is firstly positioned at a to-be-inserted portion of the skin surface of the host. When the upper casing 10 is not depressed, the insertion limiting structure (A) that is formed between the buckle portions 335 of the insertion seat 33 and the stopping portions 314 of the main body 31 maintains the insertion seat 33 at the pre-insertion position. Referring to FIGS. 8 and 9, when the upper casing 10 is depressed toward the skin surface, the buckle portions 335 of the insertion seat 33 are respectively pushed by the urging portions 123 of the upper casing 10 to be deformed inwardly and to be respectively separated from the stopping portions 314 of the main body 31, so that the insertion limiting structure (A) is collapsed. At the same time, the body engaging structures 311 of the main body 31 respectively engage the lining engaging structure 124 of the cover body 12, so that the upper casing 10 is positioned relative to the main body 31.

Figure 10:
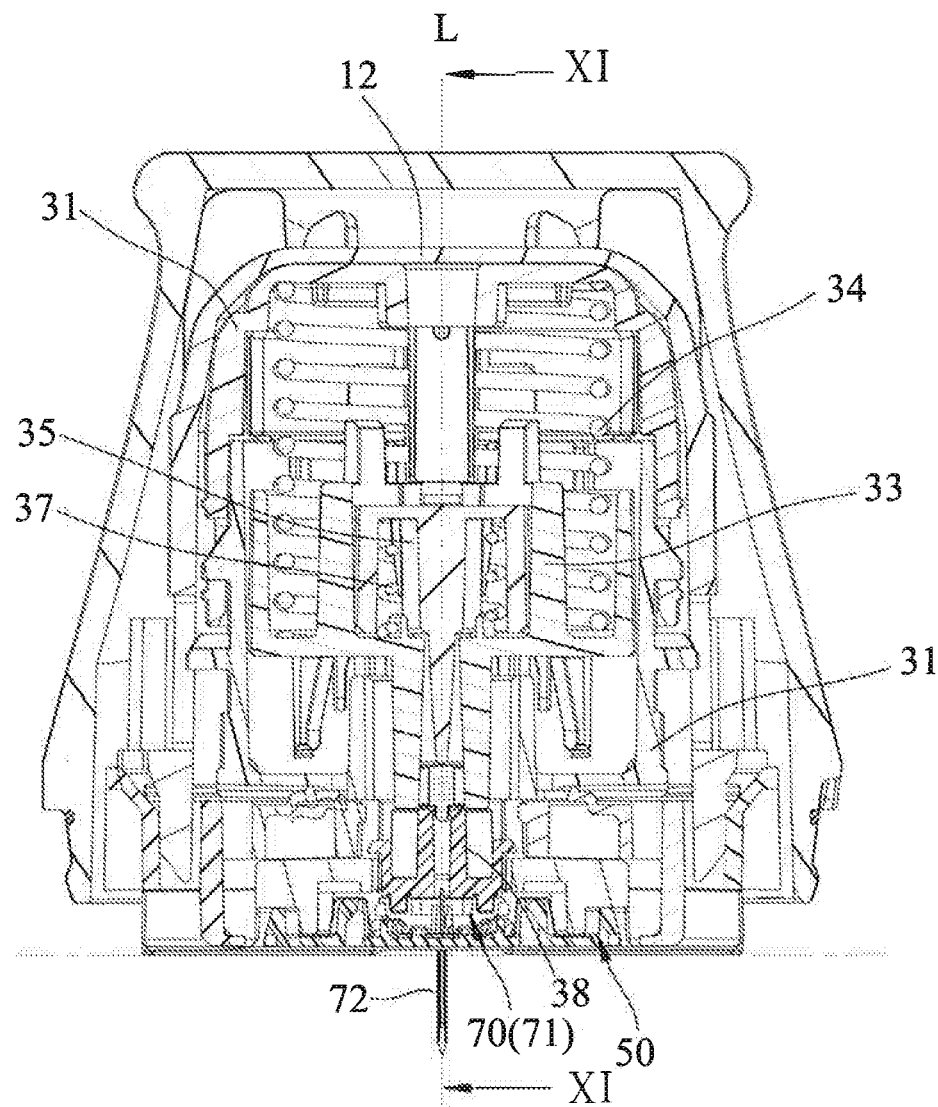
FIG. 10 is a sectional view illustrating an insertion seat of the first embodiment at an insertion position.
Figure 11:
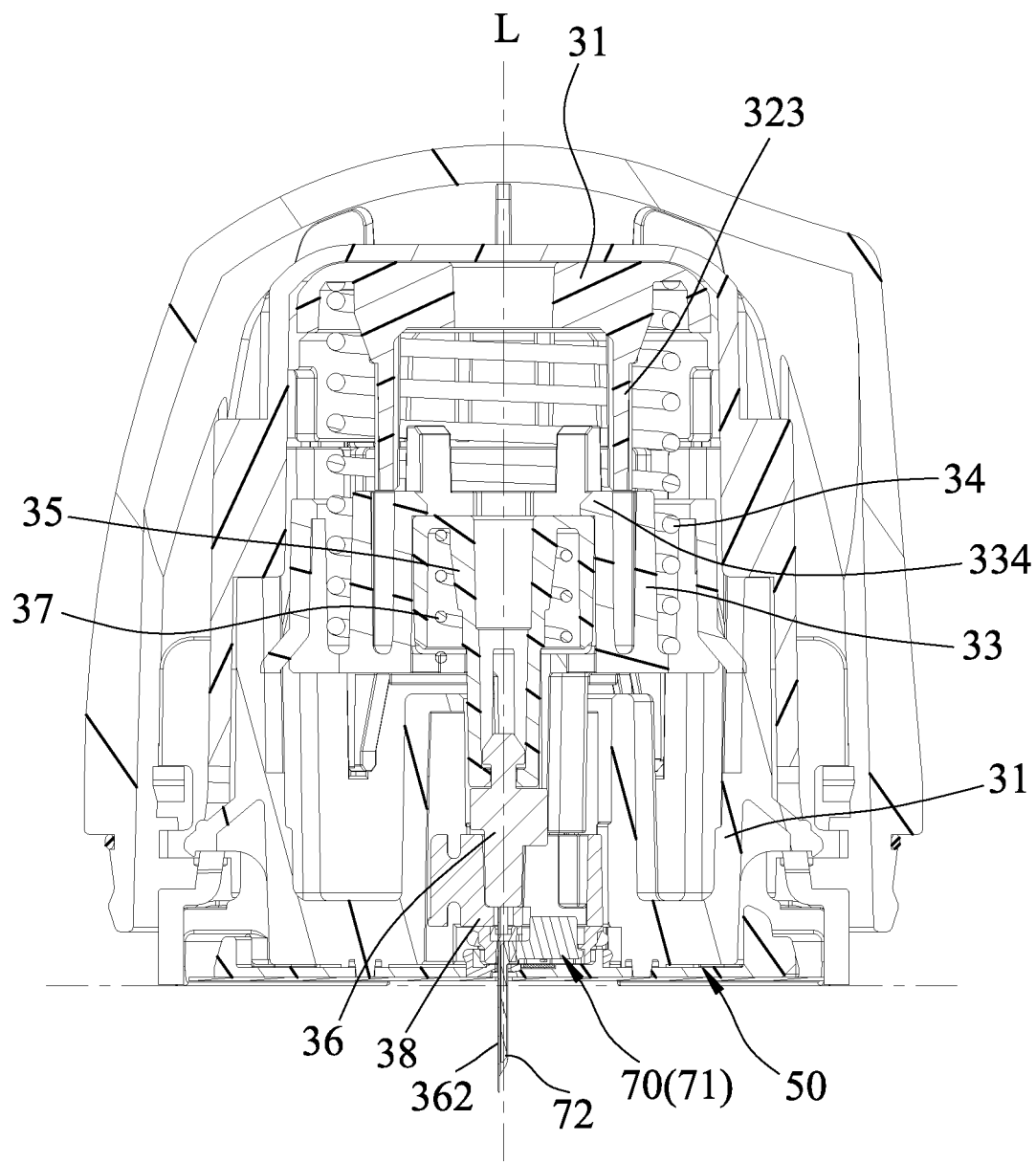
FIG. 11 is a sectional view taken along line XI-XI in FIG. 10.
Figure 12:
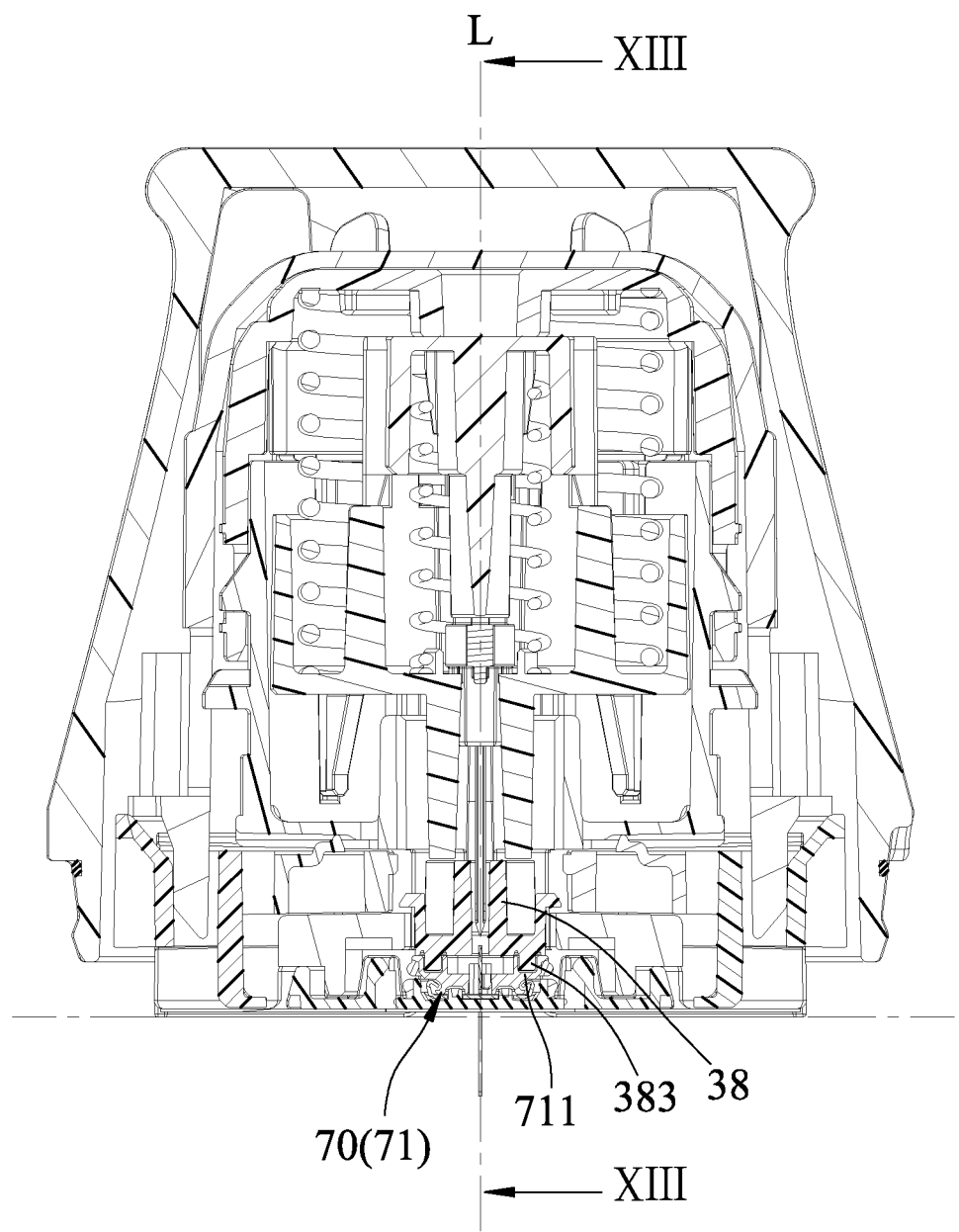
FIG. 12 is a sectional view illustrating a retraction seat of the first embodiment being retracted.
Figure 13:
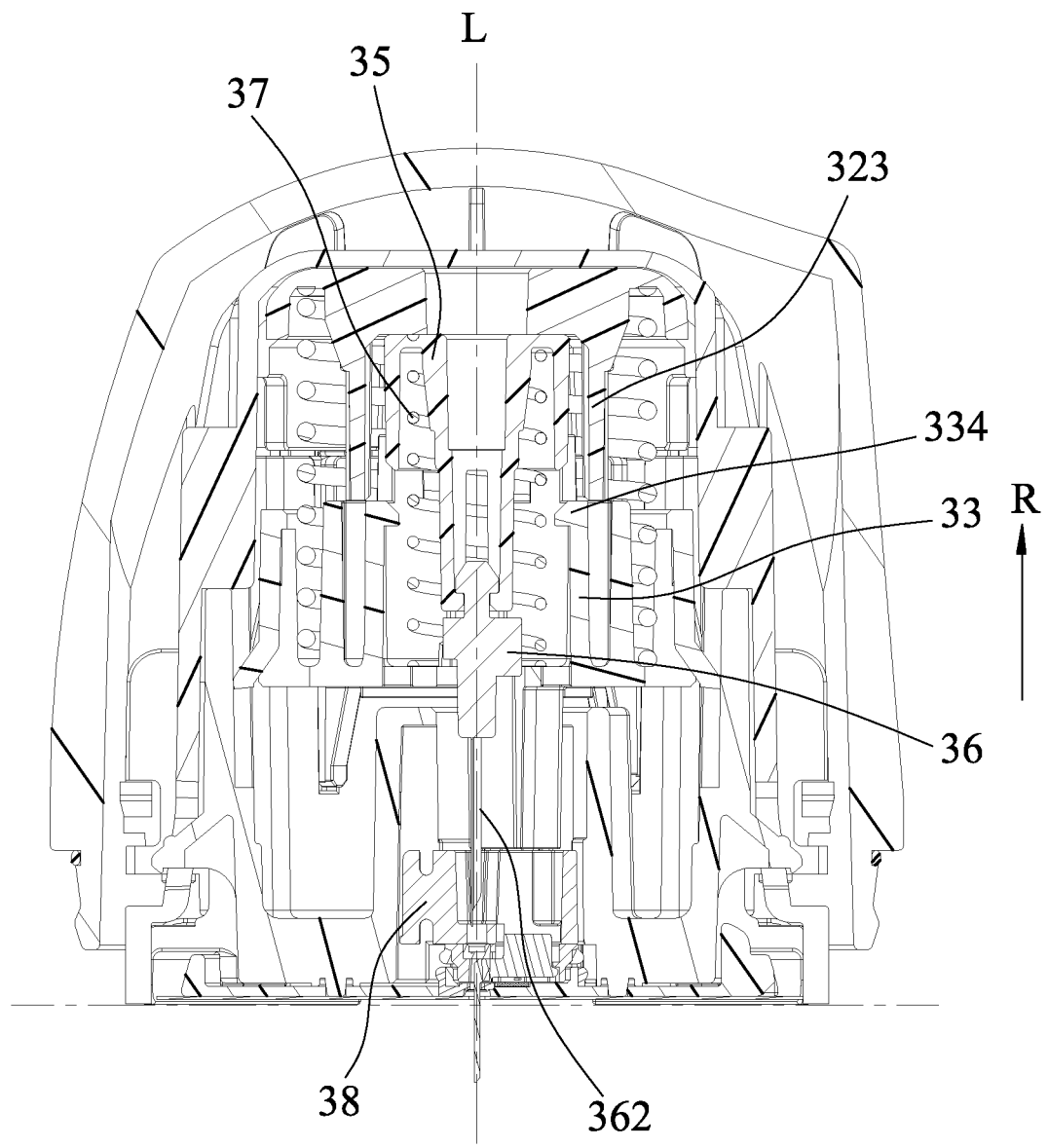
FIG. 13 is a sectional view taken along line XIII-XIII in FIG. 12.
Figure 14:
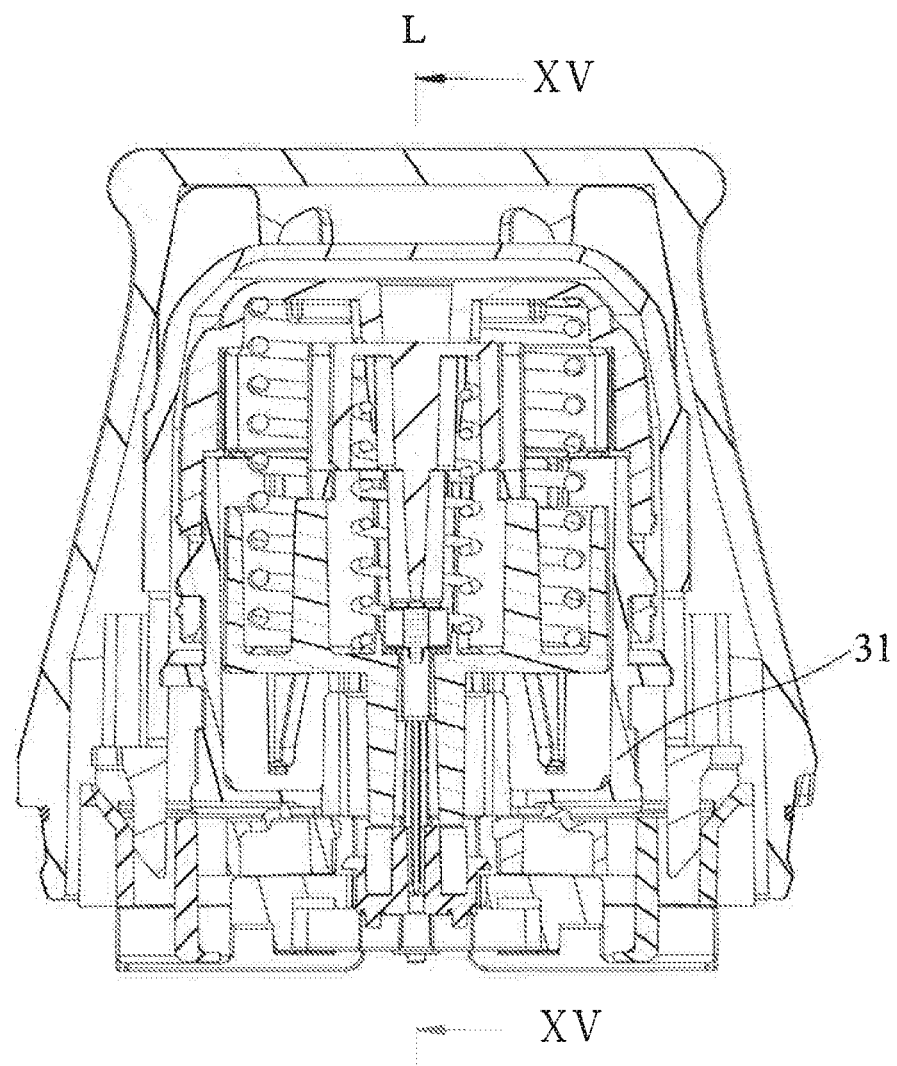
FIG. 14 is a sectional view illustrating the first embodiment in a separated state.
Figure 15:
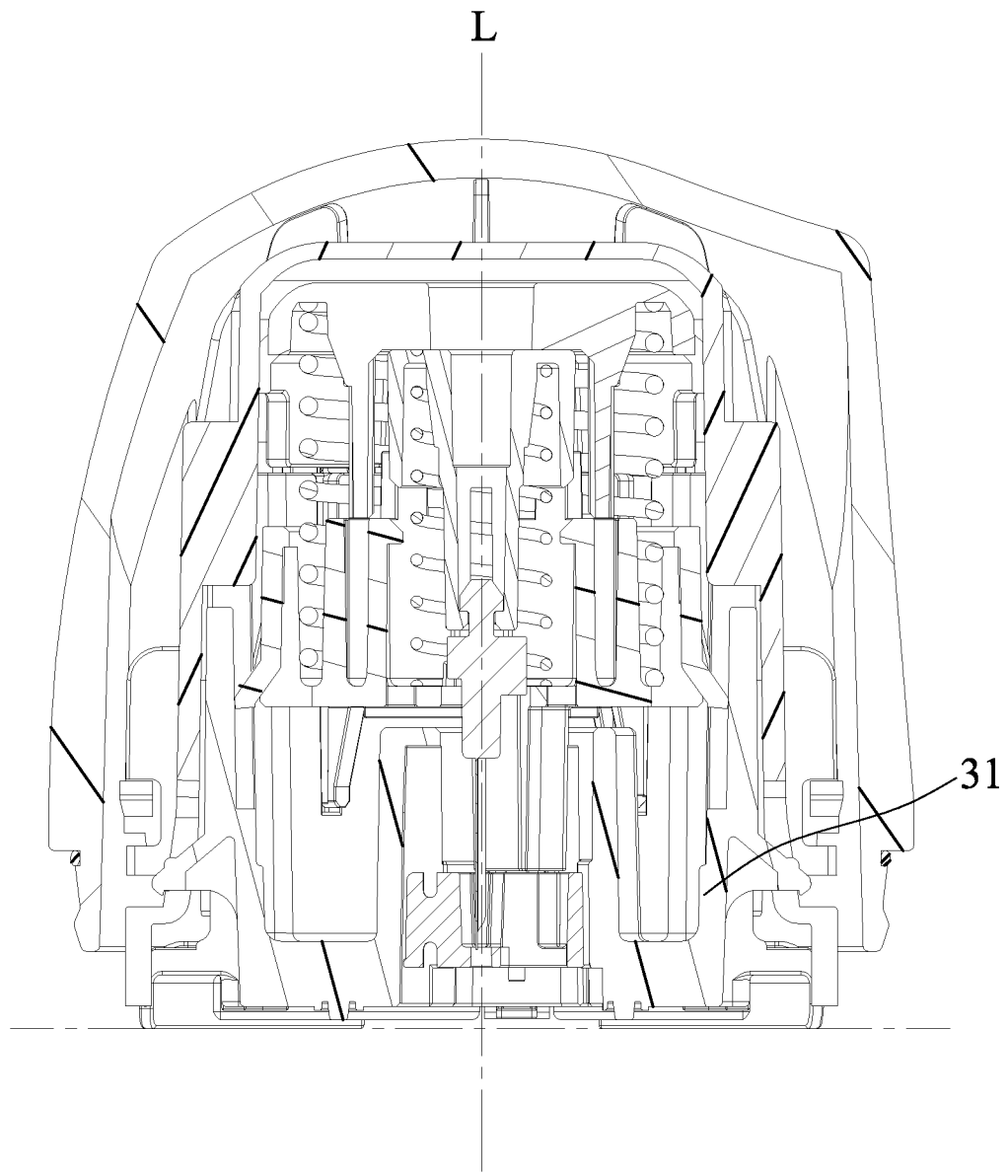
FIG. 15 is a sectional view taken along line XV-XV in FIG. 14.

Referring to FIGS. 10 and 11, after the insertion limiting structure (A) is collapsed, the restoring force of the first elastic member 34 is permitted to be released, and moves the insertion seat 33 to an insertion position to implement automatic-insertion, such that the sensor assembly 70 is moved by the insertion seat 33 to a post-insertion position, that a portion of the sensor 72 is inserted underneath the skin surface, and that the sensing seat 71 is positioned onto the mounting portion 500 of the base 50. After the sensor 72 is inserted underneath the skin surface, the limiting member 323 of the main cover 32 is separated from the retraction positioning portions 334 of the insertion seat 33, so that the retraction positioning portions 334 are permitted to be deformed outwardly to collapse the retraction limiting structure (B). As such, the restoring force of the second elastic member 37 is permitted to be released, and drives the retraction seat 35 to move in a retraction direction (R) past the retraction positioning portions 334 of the insertion seat 33 away from the skin surface, such that the insertion needle assembly 36 is separated from the auxiliary insertion seat 38 and is retracted into the insertion seat 33 to hide the insertion needle 362 thereof and to implement automatic-retraction (see FIGS. 12 and 13). The coupling protrusions 383 of the auxiliary insertion seat 38 remains fitted into the coupling recesses 711 of the sensing seat 71 so that the auxiliary insertion seat 38 is connected to the sensing seat 71 of the sensor assembly 70. The sensor assembly 70 is positioned into the base 50 during the insertion operation, and the base 50 is adhered to the skin surface by virtue of an adhesive pad 52 thereof (referring to FIGS. 14 and 15, the base 50 having been separated from the bottom portion of the main body 31).

Figure 16:
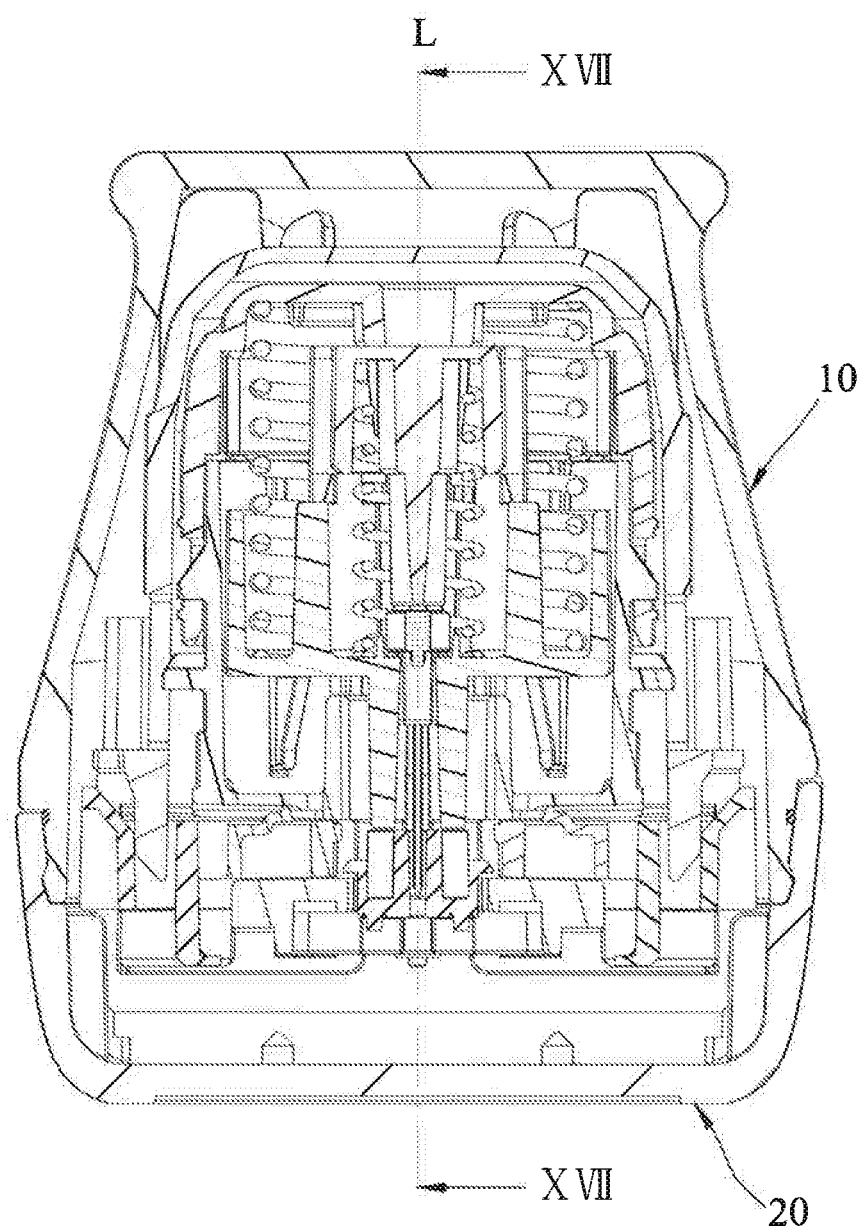
FIG. 16 is a sectional view illustrating the lower casing being re-coupled to the upper casing.
Figure 17:
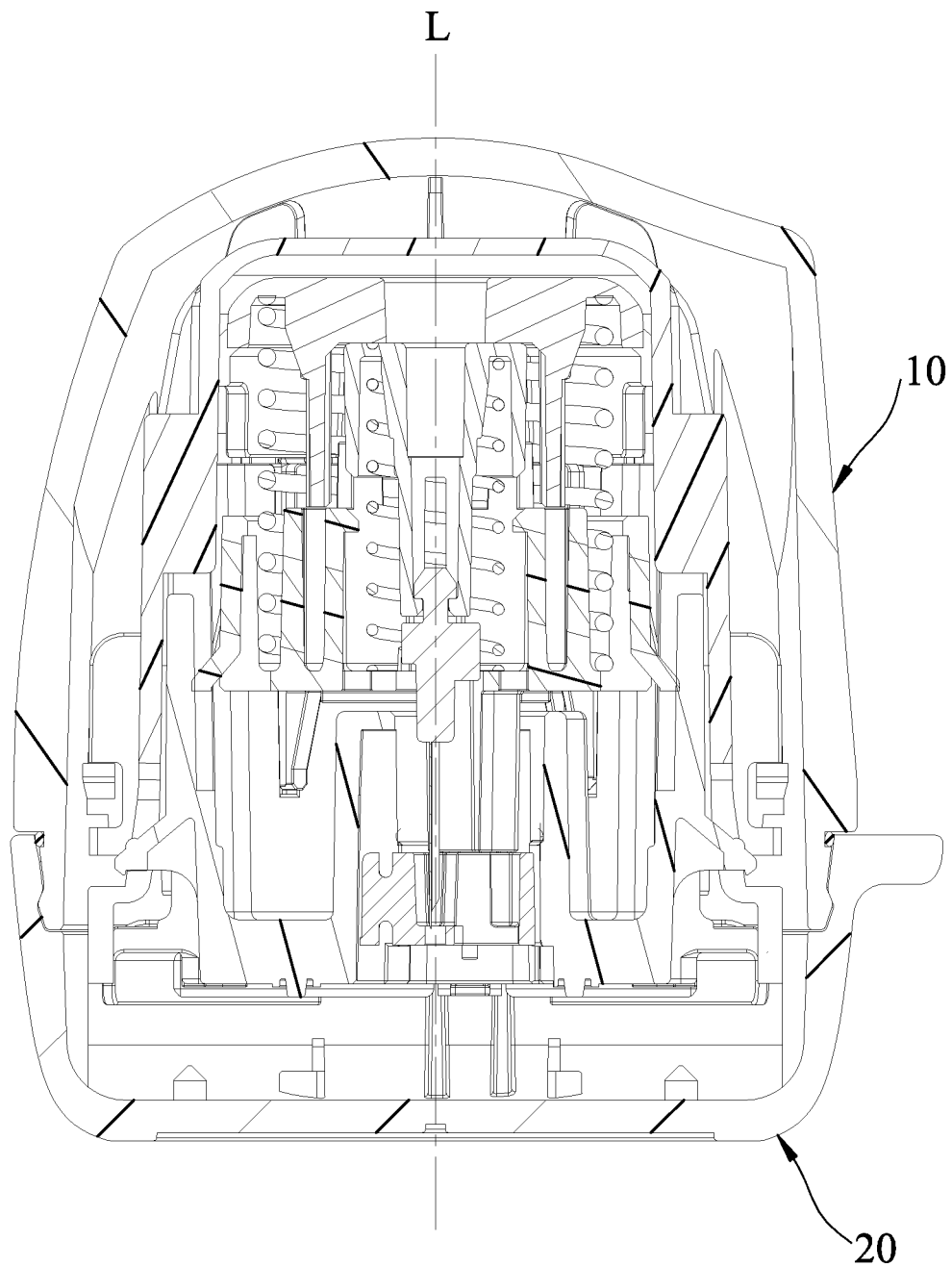
FIG. 17 is a sectional view taken along line XVII-XVII in FIG. 16.

Referring to FIGS. 16 and 17, after the insertion operation is accomplished, the separated lower casing 20 can be re-coupled to the upper casing 10, such that the used insertion device can be disposed in compliance with standard of discard of medical waste.

Referring to FIGS. 3 to 5 and 18, during the insertion, an initial speed of the insertion needle assembly 36 is insufficient to ensure that the insertion needle 362 is parallel to the insertion direction (F). At this time, the contact among the protruding portions 385 of the wing portions 382 and the wall surfaces 315 of the slide grooves 313 serves to position the insertion needle 362 such that the insertion needle 362 is parallel to the insertion direction (F). After the the insertion needle assembly is accelerated to provide the insertion straightness, and prevent the insertion needle 362 from being oblique to the insertion direction (F), the protruding portions 385 of the wing portions 382 are separated from portions of the wall surfaces 315 of the slide grooves 313 that gradually widened along an insertion direction (F). Accordingly, the insertion needle 362 can be guided stably in the initial stroke distance (H), and then is supported by the skin surface when the insertion needle 362 contacts the skin surface after the initial stroke distance (H) so as to be steadily and rapidly inserted underneath the skin surface. By virtue of the notches 384 of each wing portion 382, each wing portion 382 is compressible in the radial direction of the auxiliary insertion seat 38, and generates a restoring force in the radially outward direction after being compressed. In addition, the protruding portions 385 of the wing portions 382 abuts against the wall surfaces 315 of the slide grooves 313 to position the insertion needle assembly 36, such that the insertion needle 362 is prevented from being oblique to the insertion direction (F), and that the insertion needle 362 can be steadily inserted into the host to reduce discomfort of the host.

Figure 19:
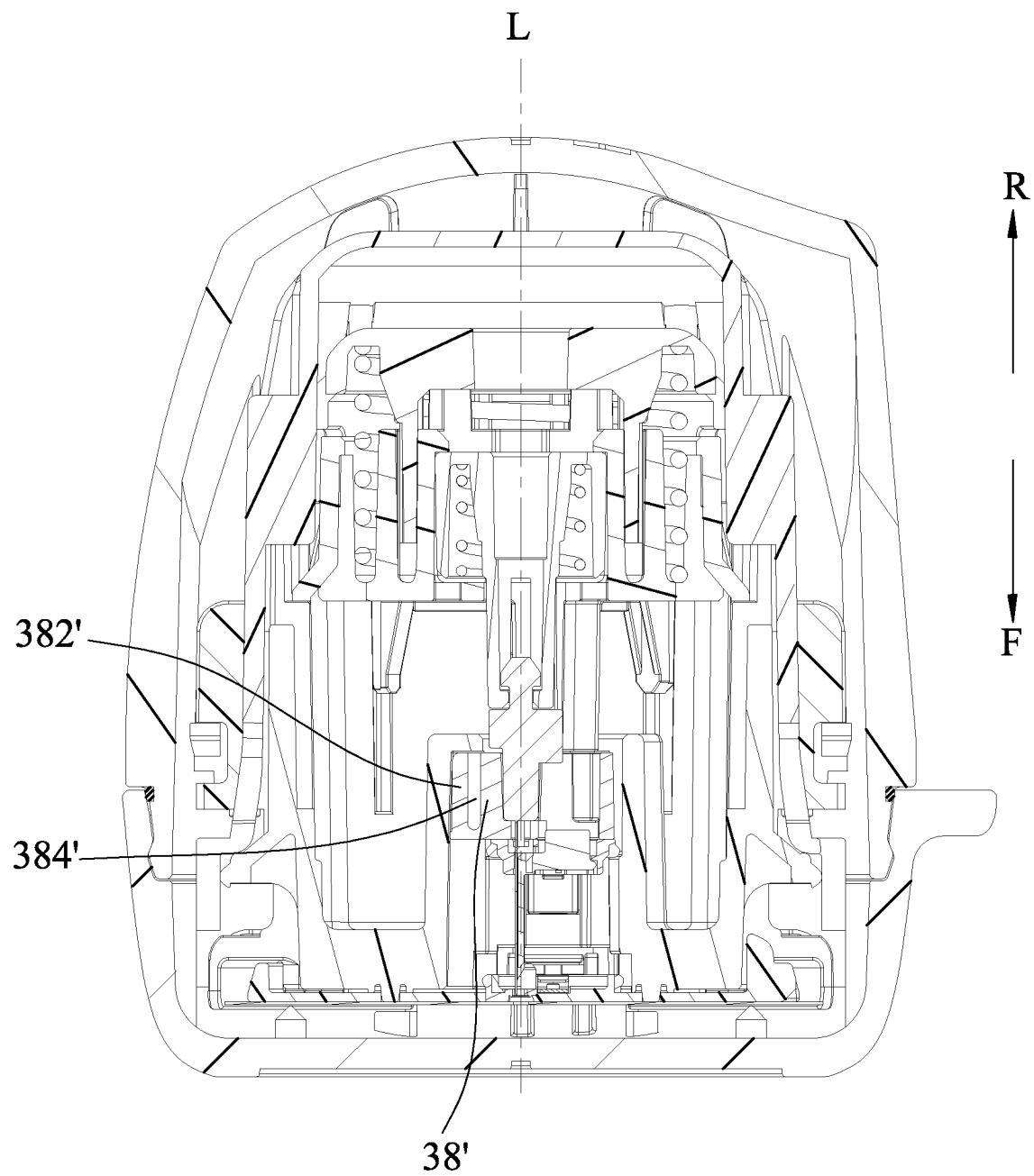
FIG. 19 is a sectional view illustrating a second embodiment of the insertion device according to the disclosure.

Referring to FIG. 19, a second embodiment of the insertion device according to the disclosure is different form the first embodiment in that: each of the wing portions 382' of the auxiliary insertion seat 38' has a notch 384' that opens upwardly. The notch 384' of each wing portion 382' is indented downwardly from a top portion of the wing portion 382', such that each wing portion 382' is compressible in the radial direction of the auxiliary insertion seat 38' perpendicular to the axial line (L), and generates a restoring force in a radially outward direction after being compressed.

Figure 20:
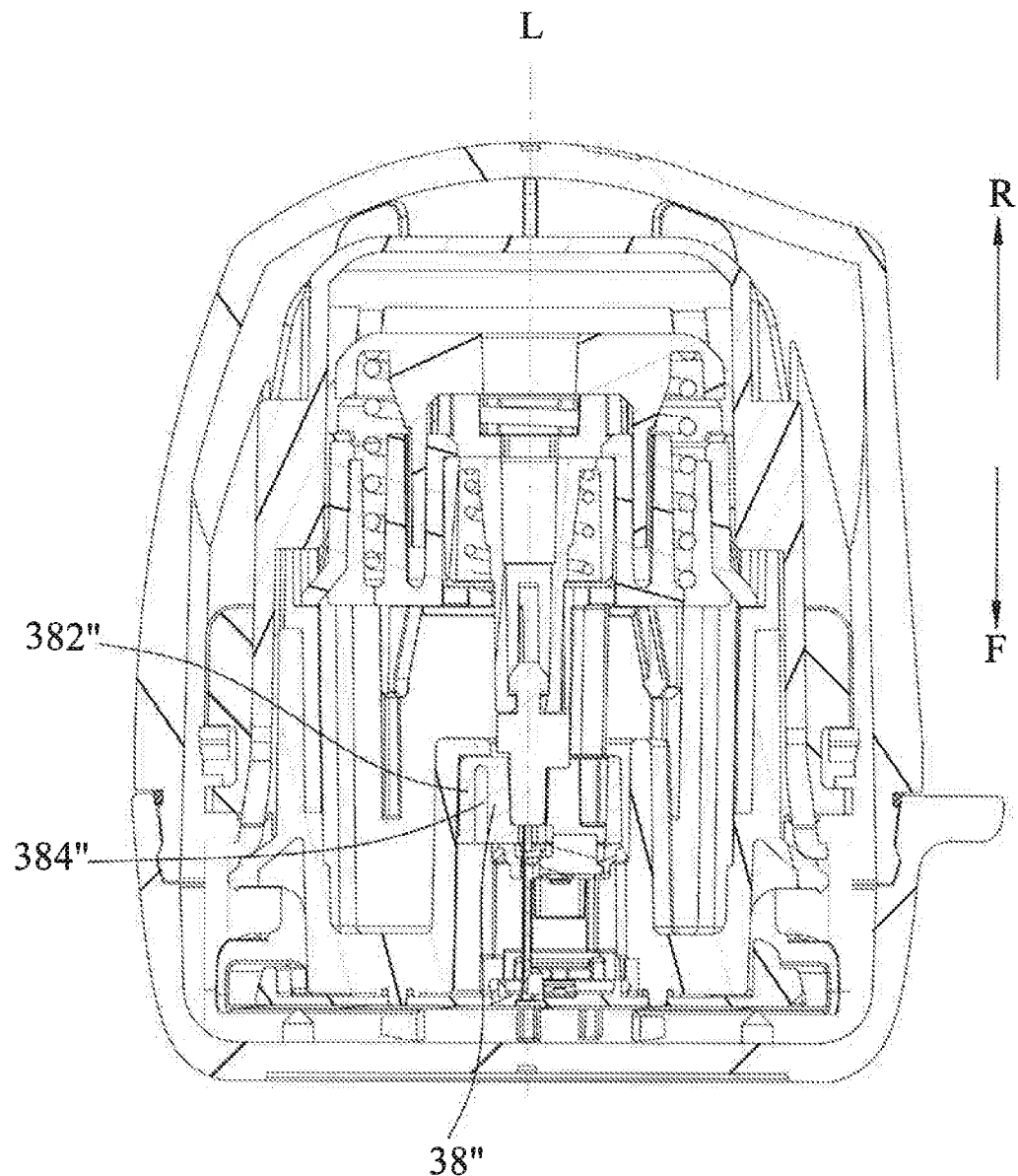
FIG. 20 is a sectional view illustrating a third embodiment of the insertion device according to the disclosure.

Referring to FIG. 20, a third embodiment of the insertion device according to the disclosure is different form the first embodiment in that: each of the wing portions 382" of the auxiliary insertion seat 38" has a notch 384" that opens downwardly. The notch 384" of each wing portion 382" is indented upwardly from a bottom portion of the wing portion 382", such that each wing portion 382" is compressible in the radial direction of the auxiliary insertion seat 38" perpendicular to the axial line (L), and generates a restoring force in a radially outward direction after being compressed.

In summary, the insertion needle assembly 36 of the insertion module 30 is assembled with the auxiliary insertion seat 38, and is positioned via the contact among the protruding portions 385 of the wing portions 382 and the wall surfaces 315 of the slide grooves 313, such that the insertion needle 362 can be guided stably in the initial stroke distance (H), and is prevented from being oblique to the insertion direction (F) so as to reduce discomfort of the host.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. An insertion module comprising:
    a main body having an accommodating hole extending along an axial line, and a plurality of slide grooves disposed on said accommodating hole around the axial line and communicating with said accommodating hole;
    an auxiliary insertion seat having a base portion, and a plurality of wing portions connected to said base portion, wherein each of said wing portions is reciprocated within a respective one of said slide grooves and has a protruding portion;
    an insertion needle assembly including a needle seat assembled with said base portion of said auxiliary insertion seat, and an insertion needle connected to said needle seat, wherein a distance between a tip end of said insertion needle and a skin surface of a host is defined as an initial stroke distance; and
    a sensor assembly including a sensing seat, and a sensor held within said sensing seat, wherein said sensing seat is assembled with said base portion of said auxiliary insertion seat, and said insertion needle is inserted through said sensing seat to cover said sensor;
    wherein each of said slide grooves has a wall surface that faces the axial line, said protruding portion of each of said wing portions resiliently abutting against said wall surface of a respective one of said slide grooves in point-contact, and said wall surface of each of said slide grooves being gradually widened along an insertion direction such that said auxiliary insertion seat is fixed before an inserting operation through an interference between said protruding portions and said wall surfaces and that said insertion needle moves stably and is prevented from being oblique relative to the insertion direction in said initial stroke distance.

2. The insertion module as claimed in claim 1, wherein each of said wing portions of said auxiliary insertion seat has a notch that opens upwardly, said notch of each wing portion being indented downwardly from a top portion of said wing portion.

3. The insertion module as claimed in claim 1, wherein each of said wing portions of said auxiliary insertion seat has a notch that opens downwardly, said notch of each wing portion being indented upwardly from a bottom portion of said wing portion.

4. The insertion module as claimed in claim 1, wherein each of said wing portions of said auxiliary insertion seat has two notches, said notches of each wing portion being respectively formed at top and bottom portions of said wing portion.

5. The insertion module as claimed in claim 1, wherein the number of said slide grooves of said main body is two, and the number of said wing portions of said auxiliary insertion seat is two.

6. The insertion module as claimed in claim 1, wherein the number of said slide grooves of said main body is three, and the number of said wing portions of said auxiliary insertion seat is three.

7. The insertion module as claimed in claim 1, wherein said slide grooves of said main body are equally spaced apart from each other around the axial line, and said wing portions of said auxiliary insertion seat are equally spaced apart from each other around the axial line.

8. The insertion device as claimed in claim 1, wherein said wall surface of each of said slide grooves and a direction of said axial line forms an angle that ranges from 0 degrees to 3 degrees.

9. The insertion module as claimed in claim 1, wherein said wall surface of each of said slide grooves and a direction of said axial line form an angle that ranges from 0 degrees to 3 degrees.

10. The insertion module as claimed in claim 1, wherein the initial stroke distance is less than 1 millimeter.

11. An insertion device comprising:
    an actuation module including a cover body, a main cover received in said cover body, an insertion seat connected to said main cover, a first elastic member abutted against said main cover and said insertion seat, a retraction seat disposed between said main cover and said insertion seat, and a second elastic member abutted against said retraction seat and said insertion seat; and
    an insertion module including:
        a main body that has an accommodating hole extending along an axial line, and a plurality of slide grooves disposed on said accommodating hole around the axial line and communicating with said accommodating hole;
        an auxiliary insertion seat having a base portion, and a plurality of wing portions connected to said base portion, wherein each of said wing portions is reciprocated within a respective one of said slide grooves and has a protruding portion;
        an insertion needle assembly including a needle seat assembled with said base portion of said auxiliary insertion seat, and an insertion needle connected to said needle seat, wherein a distance between a tip end of said insertion needle and a skin surface of a host is defined as an initial stroke distance; and
        a sensor assembly including a sensing seat, and a sensor held within said sensing seat, wherein said sensing seat is assembled with said base portion of said auxiliary insertion seat, and said insertion needle is inserted through said sensing seat to cover said sensor;
        wherein each of said slide grooves has a wall surface that faces the axial line, said protruding portion of each of said wing portions resiliently abutting against said wall surface of a respective one of said slide grooves in point-contact, and said wall surface of each of said slide grooves being gradually widened along an insertion direction such that said auxiliary insertion seat is fixed before an inserting operation through an interference between said protruding portions and said wall surfaces and that said insertion needle moves stably and is prevented from being oblique relative to the insertion direction in said initial stroke distance.

12. The insertion device as claimed in claim 11, wherein each of said wing portions of said auxiliary insertion seat has a notch that opens upwardly, said notch of each wing portion being indented downwardly from a top portion of said wing portion.

13. The insertion device as claimed in claim 11, wherein each of said wing portions of said auxiliary insertion seat has a notch that opens downwardly, said notch of each wing portion being indented upwardly from a bottom portion of said wing portion.

14. The insertion device as claimed in claim 11, wherein each of said wing portions of said auxiliary insertion seat has two notches, said notches of each wing portion being respectively formed at top and bottom portions of said wing portion.

15. The insertion device as claimed in claim 11, wherein the number of said slide grooves of said main body is two, and the number of said wing portions of said auxiliary insertion seat is two.

16. The insertion device as claimed in claim 11, wherein the number of said slide grooves of said main body is three, and the number of said wing portions of said auxiliary insertion seat is three.

17. The insertion device as claimed in claim 11, wherein said slide grooves of said main body are equally spaced apart from each other around the axial line, and said wing portions of said auxiliary insertion seat are equally spaced apart from each other around the axial line.

18. The insertion device as claimed in claim 11, wherein the initial stroke distance is less than 1 millimeter.

* * * * *